United States Patent [19]

Pinsky et al.

[11] Patent Number: 5,513,101
[45] Date of Patent: Apr. 30, 1996

[54] RADIOLOGICAL IMAGE INTERPRETATION APPARATUS AND METHOD

[75] Inventors: Howard Pinsky, Mansfield; Scott S. Sheldon, Boston, both of Mass.; Nicholas A. Christakis, Philadelphia, Pa.; Michael Schmertzler, New Caanan, Conn.

[73] Assignee: Access Radiology Corporation, Waltham, Mass.

[21] Appl. No.: 474,374

[22] Filed: Jun. 7, 1995

Related U.S. Application Data

[63] Continuation of Ser. No. 158,140, Nov. 26, 1993.

[51] Int. Cl.$^6$ .................................................. G06F 159/00
[52] U.S. Cl. ............................................ 364/401; 395/924
[58] Field of Search .............................. 364/401, 419.19, 364/146, 188, 189; 395/155, 156, 161, 200, 924

[56] References Cited

U.S. PATENT DOCUMENTS

| | | | |
|---|---|---|---|
| 4,764,870 | 8/1988 | Haskin | 364/415 |
| 4,833,625 | 5/1989 | Fisher et al. | 364/518 |
| 4,958,283 | 9/1990 | Tawara et al. | 364/413.13 |
| 5,005,126 | 4/1991 | Haskin | 364/413.13 |
| 5,077,768 | 12/1991 | Shigyo et al. | 378/98 |
| 5,101,476 | 3/1992 | Kukla | 395/200 |
| 5,216,596 | 6/1993 | Weinstein | 364/413.02 |
| 5,231,572 | 7/1993 | Shigyo et al. | 364/413.01 |
| 5,235,510 | 8/1993 | Yamada et al. | 364/413.02 |
| 5,249,290 | 9/1993 | Heizer | 395/650 |
| 5,272,625 | 12/1993 | Nishihara et al. | 364/413.13 |

FOREIGN PATENT DOCUMENTS

| | | |
|---|---|---|
| 0487110A2 | 5/1992 | European Pat. Off. . |
| 0599097A2 | 6/1994 | European Pat. Off. . |
| 3823251A1 | 1/1989 | Germany . |

OTHER PUBLICATIONS

"New High–Resolution Teleradiology System: Prospective Study Of Diagnostic Accuracy In 685 Transmitted Clinical Cases," Goldberg et al., *Radiology*, Feb. 1993, pp. 429–434.
"Cost–Effectivness Of Teleradiology For Rural Hospitals", Hilsenrath et al., *Applied Radiology*, Dec. 1992, pp. 54–58.
"Wide Area Network Strategies For Teleradiology Systems," Dwyer et al., *RadioGraphics*, May 1992, vol. 12, No. 3, pp. 567–576.
"Teleradiology System Analysis Using A Discrete Event Driven Block Oriented Network Simulator," Stewart et al., *SPIE*, vol. 1654, Medical Imaging VI: PACS Design and Evaluation, 1992, pp. 2–13.

(List continued on next page.)

*Primary Examiner*—Donald E. McElheny, Jr.
*Attorney, Agent, or Firm*—Testa, Hurwitz & Thibeault

[57] ABSTRACT

A Radiology Healthcare Network provides high quality, timely medical interpretations of radiological images on a national (e.g., across the U.S.) and regional basis. The images can include images created by conventional x-ray technology, computed radiography, magnetic resonance imaging (MRI), computed tomography (CT), ultrasound imaging, nuclear medicine, and mammography equipment. The invention includes the acquisition of these images from health care facilities, the conversion of these images to digital format, the routing of these converted images, the interpretation of these routed images, and the routing of the interpretations back to the originating facility. The images are routed-(e.g., on a variety of high-speed digital and analog telecommunication networks) to the appropriate interpretation resource by an administrative site on the Network based on one or more requirements associated with the radiological study. The interpretation can be performed on high-resolution workstations and/or on films produced by film printers. The invention can include quality control measures which assure high image and interpretation quality. The control and tracking of images by the administrative site results in the production of a complete, signed interpretive report in a timely manner.

22 Claims, 5 Drawing Sheets

OTHER PUBLICATIONS

"Design of a High-Speed, High-Resolution Teleradiology System," Stewart et al., *SPIE*, vol. 1654, Medical Imaging VI: PACS Design and Evaluation, pp. 66–80.

"Command-Wide Teleradiology For US Armed Forces In Korea," Mun et al., *SPIE*, vol. 1654, Medical Imaging VI: PACS Design and Evaluation, pp. 81–88.

"Wide Area Networks For Teleradiology," Baxter et al., *Journal Of Digital Imaging*, vol. 4, No. 1, Feb. 1991, pp. 51–59.

"Design of a Medical Image Management System: A Practical Cost-Effective Approach," Seshadri et al., *Computer Methods and Programs In Biomedicine*, vol. 25, 1987, pp. 185–192.

"Queueing Analysis: A Useful Planning And Management Technique For Radiology," Rosenquist, *Journal of Medical Systems*, vol. 11, No. 6, 1987, pp. 413–419.

"Fundamental Properties of Digital Images," Balter, *RadioGraphics*, Jan. 1993, vol. 13, No. 1, pp. 129–141.

"Local Area Network Topologies, Media, and Routing," Stewart, *RadioGraphics*, May 1992, vol. 12, No. 3, pp. 549–566.

"A Modular, Flexible and Expandable High-Performance Image Archiving And Retrieving Open-Architecture System," Chen, *SPIE*, vol. 1654, Medical Imaging VI: PACS Design and Evaluation, 1992, pp. 208–211.

"Realism v. Optimality: A Systems-Engineered Wide Area Network Design System," Sykes et al., *IEEE*, 1991, pp. 785–794.

"Asynchronous Transfer Mode Or Synchronous Transfer Mode Or Both?" Aaron et al., *IEEE Communications Magazine*, Jan. 1991, pp. 10–13.

"A Scheme For Real-Time Channel Establishment In Wide-Area Networks," Ferrari, *IEEE Journal On Selected Areas In Communications*, vol. 8, No. 3, Apr. 1990, pp. 368–379.

"Routing and Flow Control in High-Speed Wide-Area Networks," Maxemchuk, *Proceedings of the IEEE*, vol. 78, No. 1, Jan. 1990, pp. 204–221.

"Performance Analysis Of a LAN/WAN Bridging Architecture," Rodrigues et al., IEEE, 1989, pp. 0646–0650.

"Kodak Ektascan Imagelink Systems" brochure, 6 pages, Apr. 1992, Eastman Kodak Co., Health Services Division, Rochester, NY.

"Lumiscan Operator's Reference Guide For Models 150 and 200," 90 pages, Jul. 1992, LUMISYS, Sunnyvale, CA.

Kotsopoulos et al., "A New Medical Data Management Concept in Hybrid Cellular Mobile Radio Communication Network"; *IEEE Global Telecommunications Conference, Globecom '91*, 674–680 (1991).

Martinez et al., "Imagenet: A Global Distributed Database For Color Image Storage and Retrieval In Medical Imaging Systems"; *Fifth Annual IEEE Symposium on Computer-Based Medical Systems;* 710–719 (1992).

Picand et al., "Le Project Sirene d'Imagerie Medicale: Conclusions Techniques Du CCETT"; *L'Onde Electrique;* 71:19–25 (1991).

Sheng et al., "The Design of Medical Image Databases: A Distributed Approach"; *Ninth Annual International Phoenix Conference on Computers and Communications;* 288–295 (1990).

"A Modern Fully Integrated Hospital Information System" by Milan et al., 1992.

RADIOLOGICAL IMAGE INTERPRETATION APPARATUS AND METHOD

This is a continuation of Ser. No. 08/158,140 filed on Nov. 26, 1993.

BACKGROUND OF THE INVENTION

This invention relates to methods and apparatus for providing professional radiology interpretation services at locations distant from the healthcare facilities originating the studies in a centrally controlled and directed manner that results in the required kind of radiology service (i.e., specialty or sub-specialty radiology as necessary) delivered in a clinically effective and timely manner.

Conventional radiology services are traditionally site-based, where the healthcare facility exclusively has radiology services provided to it by an on-site radiologist or radiology group. The on-site provider of radiology services, depending on the size, kind, or location of the facility, may or may not provide the desired breadth of radiology services over the desired timeframe. For example, small, rural hospitals typically receive radiology service infrequently, by a circuit-riding radiologist responsible for covering a plurality of healthcare facilities. Another example of unmatched supply and demand for radiology services could be a non-hospital based diagnostic imaging center, where a relatively low volume of studies oftentimes makes it difficult to attract the desired or necessary specialty or sub-specialty radiology services to the diagnostic imaging center.

In view of the foregoing, it is desirable to provide a system for improving the distribution of radiology services which would result in an integrated regional and national system for standardized, centrally managed radiology services, available to all areas and types of hospitals, thereby achieving efficiency and utilization of radiologists with specialty and sub-specialty training and skills, resulting in improvements in quality and controlling costs associated with providing radiology services.

SUMMARY OF THE INVENTION

This invention provides a Radiology Healthcare Network for providing generalist, specialty, and sub-specialty, timely medical interpretations of radiological images on a national (e.g., across the U.S.) and regional basis. The images can include images created by conventional x-ray technology, computed radiography, magnetic resonance imaging (MRI), computed tomography (CT), ultrasound imaging, nuclear medicine, and mammography equipment. The invention includes the acquisition of these images from healthcare facilities, the conversion of these images to digital format, the routing of these converted images, the interpretation of these routed images, and the routing of the interpretations back to the originating facility. The images are routed (e.g., on a variety of digital and analog telecommunication networks) to the appropriate interpretation resource by an administrative site on the Network based on one or more requirements associated with the radiological study. The interpretation can be performed on workstations with medical image grade monitors, and/or on radiographic films produced by laser camera based printers. The invention can include quality control measures which assure high image and interpretation quality. The control and tracking of images by the administrative site results in the production of a complete, signed interpretive report on a timely basis.

In general, the invention relates to a method for providing interpretation of radiological images, which comprises providing an administrative site coupled to a wide area network; providing a plurality of acquiring sites coupled to the wide area network for digitizing radiological images and generating identifying information about a radiology study, the study including one or more of the images; providing a plurality of interpretation sites coupled to the wide area network which each includes interpretation resources; and utilizing the administrative site as follows. The administrative site receives identifying information about the study from one of the acquiring sites over the wide area network; determines one or more study parameters from the received study identifying information; matches the study parameters to the interpretation resources available from the interpretation sites to select one of the interpretation sites as an appropriate interpretation site to interpret the study; routes the one or more digitized radiological images onto the wide area network to the selected interpretation site; receives report information about an interpretation of the study from the selected interpretation site over the wide area network; and routes the report information to the acquiring site from which the study identifying information about the radiology study was received.

Embodiments of the invention can include the following features:

The step of determining the one or more study routing parameters can include determining a modality of the study such as computer assisted tomography, conventional x-ray imaging, computed radiography, magnetic resonance imaging, nuclear medicine, and ultrasound imaging; determining a pathology of the study, a geographic location of the acquiring site, information about a patient which is a subject of the study such as patient age and sex, or information about an anatomy of a patient which is a subject of the study; determining the requisite interpretation turnaround timeliness. The step of determining the suitable radiology resources on the Radiology Healthcare Network. The step of best matching an originated study with the best available radiology resource, according to routing parameters. The step of monitoring workflow in and out of radiology resources to ensure quality and timeliness of study interpretations.

Thus, the systems and methods according to the invention advantageously make high quality radiology interpretation services available to all areas uniformly and on an as-needed basis. Also, the invention utilizes a matrixed approach to providing radiology services which allows efficient utilization of radiological expertise and thus controls costs typically associated with providing high quality and highly specialized radiology services.

DESCRIPTION

Figure 1:
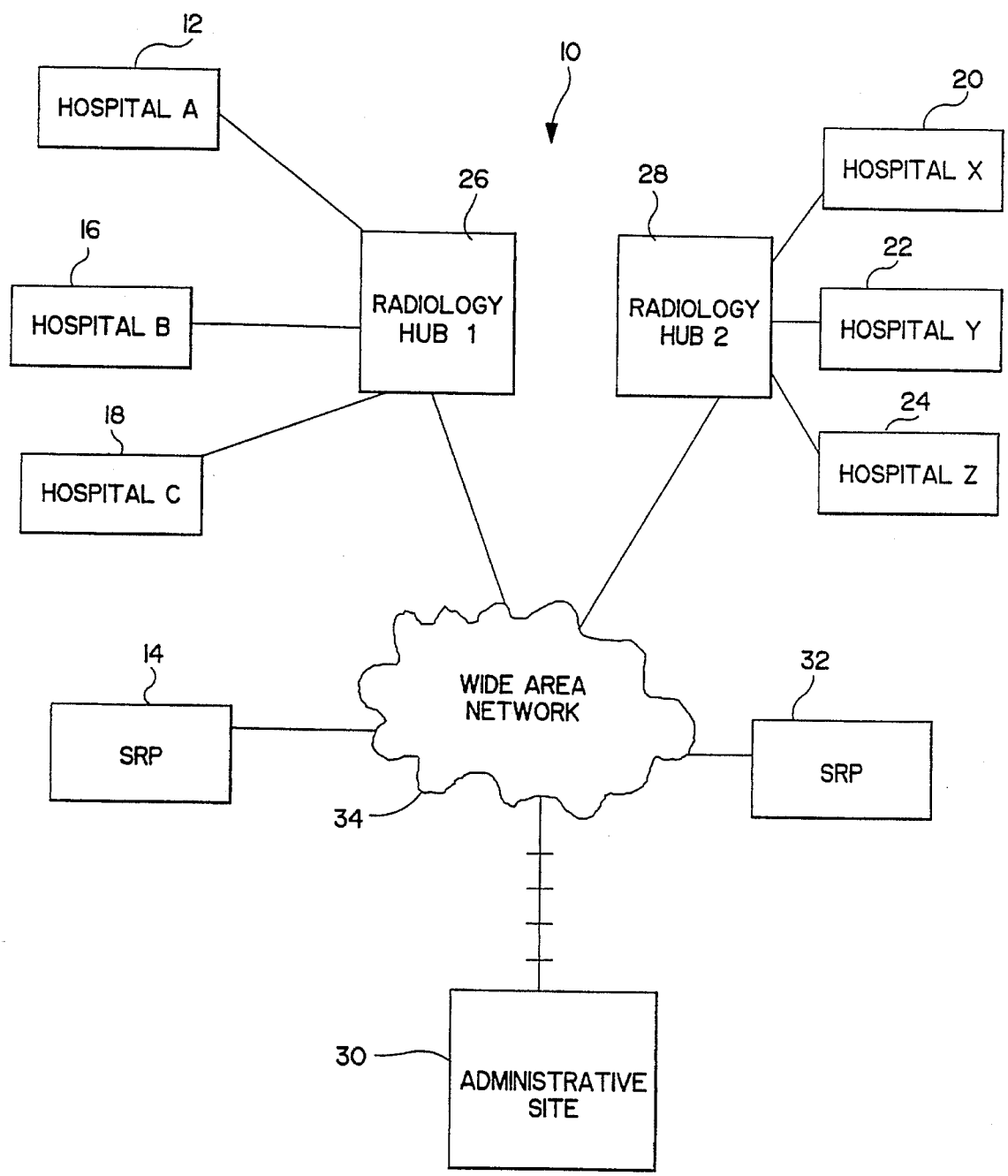
FIG. 1 is a diagram of an area communications system for providing interpretation of radiological images to remote locations according to the invention.

Referring to FIG. 1, in accordance with this invention, a Radiology Healthcare Network 10 for providing high quality generalist, specialty, and sub-specialty and timely medical interpretations of radiological images on a national or regional basis includes a plurality of acquiring sites 12, 16, 18, 20, 22 and 24 for acquiring radiological images and requesting radiological studies of those images, one or more radiology hubs 26, 28 for providing general and specialty radiological interpretation, one or more Strategic Radiology Partners (SRPs) 14, 32 for providing highly specialized (sub-specialty) radiological interpretation, and one or more network administration sites ("Admin. Sites") 30 for managing and controlling the flow and quality of images and interpretations across the Radiological Healthcare Network 10 (hereinafter also referred to as the "Network").

In the disclosed embodiment, the acquiring sites can be primary care hospitals 12, 16, 18, 20, 22, 24, or other health service provider facilities such as radiologic imaging centers, individual clinics and doctor's offices, and mobile imaging services (herein collectively referred to as "acquiring sites" for simplicity).

In the disclosed embodiment, the acquiring sites transfer the acquired radiological images as studies (the "Study") typically consisting of multiple radiological images to the Radiology Healthcare Network 10 for interpretation. The Radiology Healthcare Network consists of (i) a tiered level of radiology healthcare providers who provide radiology interpretive services connected by specialized computer equipment and components designed to support medical radiologic imaging, commonly referred to as either Picture Archive Communications Systems ("PACS") or "Teleradiology," and (ii) a wide area digital telecommunications network provided by existing (Local Exchange Carriers (LEC) and Inter Exchange Carriers (IEC). The Study is routed by an Admin. Site 30 based upon the specific requirements of the Study matched against the current availability of requisite expertise from radiology healthcare providers on the Network. The Admin. Site 30 can be a single central entity, or it can be distributed among several entities on the network, determined by, for instance, workload, and redundancy for disaster recovery. The progress of the Study is monitored by the Admin. Site 30, and if not completed within certain pre-defined time-frames, the Study is re-routed by the Admin. Site to another Network radiology healthcare provider who is able to match the requirements of the Study.

Routing of Studies by the Admin. Site 30 is based upon the specific interpretive needs of the Study, such as the availability of the requisite specialty or sub-specialty radiologic staff to interpret the Study, all with a potential preference for the closest radiology healthcare provider within a specific geographic area. Specifically, Study parameters which can effect Study routing include patient demographics (e.g., age and sex), suspected pathology, imaging modality, imaged body part(s), required turnaround time of the interpretation, geography, and Study type (e.g., routine diagnostic interpretation, stat interpretation, quality assurance interpretation, overread interpretation).

Figure 3:
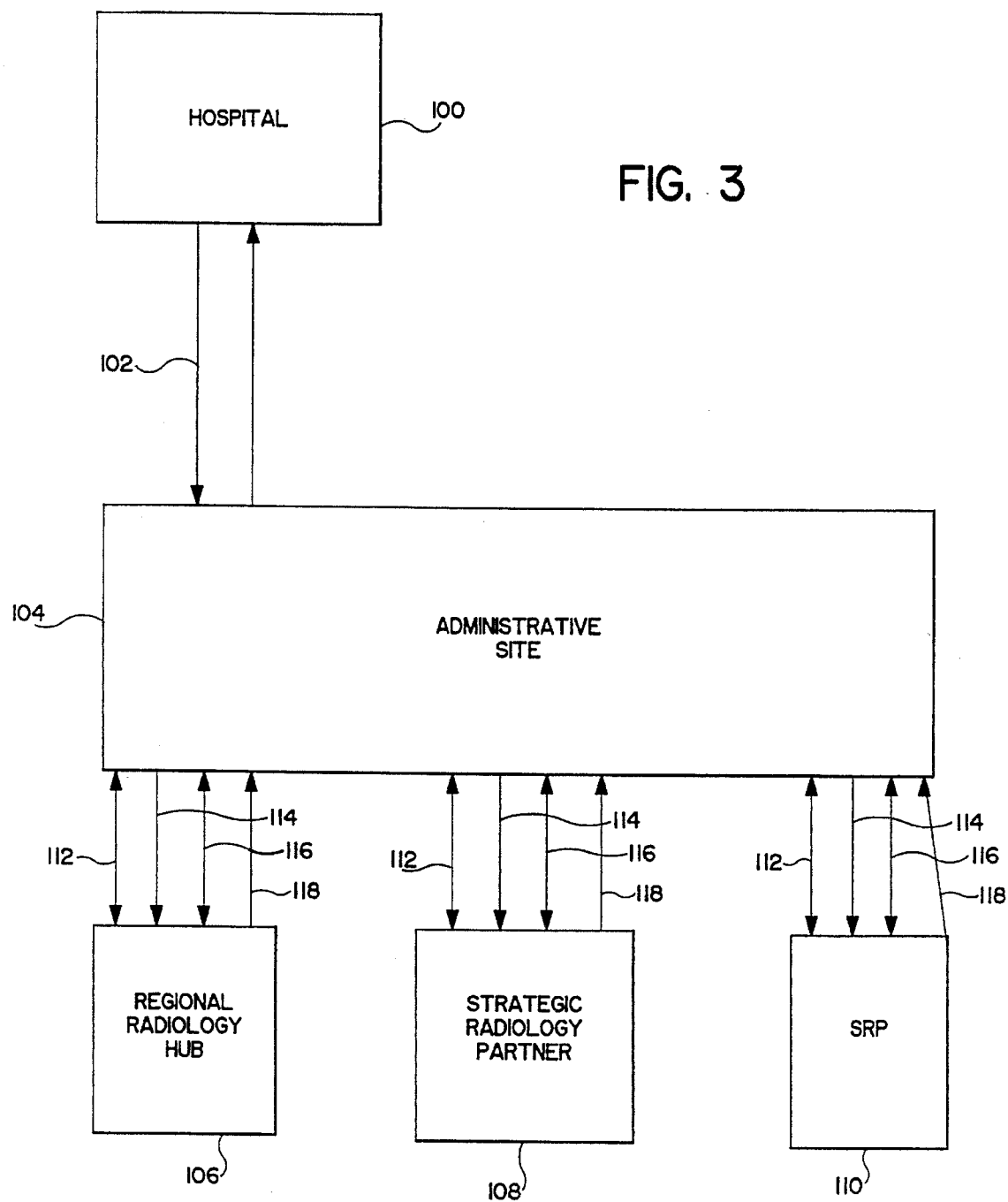
FIG. 3 is a block diagram illustrating the flow of radiological studies and interpretations controlled by an administrative site.

Referring to FIG. 3, the flow of operational control of a patient radiologic Study is shown. As an initial step in the flow, an acquiring site such as a hospital 100 acquires digital representations of one or more radiological images which together form a patient radiologic Study (the "Study"). The Study typically has other information associated therewith such as the suspected pathology, the modality, the anatomy, patient-identifying data, location of the acquiring site. The associated Study information also might include the level of urgency of the Study, and other Study parameters. The associated Study information (and possibly the image data itself) is then transmitted (as indicated by arrow 102) to an Admin. Site 104. In general, the Admin. Site 104 stores all of the patient information and Study images which is transmitted to it, for example, by using storage devices capable of storing large amounts of data such as redundant arrays of independent disks (RAID) and/or optical disk jukeboxes.

After the Admin. Site 104 receives the transmission from the hospital 100, the Admin. Site 104 determines a set of Study parameters, from the associated Study information, which characterize the Study. The Admin. Site then checks the Study parameters against (as indicated by arrow 112) the resources of available Network interpretation sites, such as regional radiology hubs and/or strategic radiology partners (SRPs) in the Radiology Healthcare Network, for the best resource available for that Study. In the embodiment of FIG. 3, the interpretation sites include one regional radiology hub 106 and two SRPs 108, 110 which are coupled to the Admin. Site 104. This check by the Admin. Site 104 can include a check on (i) the availability of medical generalists, specialists, and sub-specialists, (ii) the types of such available medical personnel and their hours of coverage, and (iii) the existing backlog at the hub and/or SRPs. The backlog refers to the number of Studies and/or related information which already have been sent to the hub or SRP and which have yet to be acted on by the hub or SRP. The information which the Admin. Site 104 gathers as a result of these checks is then used to determine how to route the Study from the acquiring site for interpretation.

Having made the routing determination, the Admin. Site 104 routes the Study to an electronic reading stack at the appropriate radiology hub 106 or SRP 108, 110 as indicated by arrow 114. The Admin. Site can accomplish this routing without having to actually receive the Study itself. Rather, it can direct the Network to make the appropriate connection between the acquiring site and the selected hub or SRP so that the images can be transferred directly.

The Admin. Site 104 then periodically monitors the progress being made on the Study that was routed to the radiology hub or SRP to determine whether the hub or SRP is interpreting the Study in a timely manner (as indicated by arrow 116). If the interpretation is not completed within a predetermined amount of time, the Admin. Site 104 can (i) delete the Study from the electronic reading stack of the radiology hub or SRP to which that Study was routed and then (ii) re-route that Study to a new interpretation site (e.g., radiology hub or SRP).

After the Study reaches a hub or SRP capable of rendering the necessary interpretation services in a timely manner, that hub or SRP interprets the Study and notifies the Admin. Site 104 of the existence of an interpretive report of the Study (as indicated by arrow 118). The Admin. Site 104 then can either receive the interpretation directly and route it back to the hospital 100 which acquired the Study initially or it can route the interpretation from the interpreting site to the hospital directly. The Admin. Site 104 can also receive and store a copy of the report.

Note that the interpretation site, whether it is a radiology hub or an SRP, which receives the Study in its electronic reading stack as routed by the Admin. Site 104 might not complete an interpretation of the Study for a variety of reasons. Those reasons can include (i) the fact that the Study was not received by the interpretation site with satisfactory quality; (ii) the interpretation site needs more information to complete an interpretation; or (iii) the interpretation site requires more medical expertise than is available thereat. In these situations, the interpretation site typically will (i) request a re-transmission of the Study from the Admin. Site 104; (ii) request the Admin. Site 104 to request more images and/or Studies from the hospital 100 which initially sent the Study; or (iii) request the Admin. Site 104 to delete the Study from its electronic reading stack and then route that Study to another interpretation site that has the needed expertise.

Radiology healthcare providers who provide radiology interpretive services on the Network are tiered according to the type of generalist, specialty, and sub-specialty expertise available within the institution, the number of staff within a specific expertise in the institution, and their hours of coverage.

A regional radiology hub can typically provide radiology interpretation services that are otherwise unavailable at the acquiring site, and may be a general referral site for the acquiring site, e.g., the radiology hub may be a university hospital or regional health care facility that may normally gets referrals from the acquiring site hospital. The radiological services provided by a radiology hub typically includes basic radiologic interpretation, specialty interpretation, urgent interpretation, and interpretation services at extended hours of coverage. With such a system, there does not need to be a radiologist present at the acquiring site, rather only a radiology technician capable of producing a satisfactory radiology image.

An SRP is typically a major radiology center which offers radiology services usually unavailable at the radiology hubs, such as sub-specialization, urgent interpretation, quality assurance interpretation, consultations, and expanded hours of coverage. SRPs can include larger, well-known medical centers, such as the Brigham & Womens Hospital and The Cedar Sinai Medical Center, which offer high level expertise and sub-specialty availability. In general, the SRPs have a higher level of radiological image interpretation sub-specialty expertise, more advanced radiological facilities, and higher availability than the radiology hubs. Like the radiology hubs, the SRPs interpret the radiology Study and produce reports which are directed back to the appropriate acquiring site.

Hospitals, radiology hubs, SRPs, and Admin. Sites are interconnected through a flexible high speed digital data communications network which utilizes as its backbone an existing and future contemplated, Inter Exchange Carrier (IEC) packet and cell switched wide area network 34 (WAN). It may also be possible, with acceptable compression techniques to use voice grade switched of dedicated lines to replace both the LEC and IEC portions of the Network.

In general, the WAN 34 can use "frame relay" which combines the performance of private telephone lines with the bandwidth efficiency and superior connectivity of packet switching. In short, frame relay is an advanced, packet data communications technology designed for bursty, data-intensive applications such as image transfer and client/server exchange. The WAN 34 frame relay services typically are provided by long distance carriers such as AT&T, Sprint or MCI.

Acquiring sites can be connected to an associated radiology hub through a direct high speed point-to-point connection established through a Local Exchange Carrier (LEC), such as NYNEX, or through a combination of connections through the radiology hubs and the WAN using both IEC and LEC channels. It may also be possible to use cable television network services to provide LEC and IEC network services. The flexibility of these numerous connection strategies allows for connections to be optimized based on tariffs, connection, and equipment costs, and provides a seamless network to allow for the routing of Studies on a national basis.

Figure 2A:
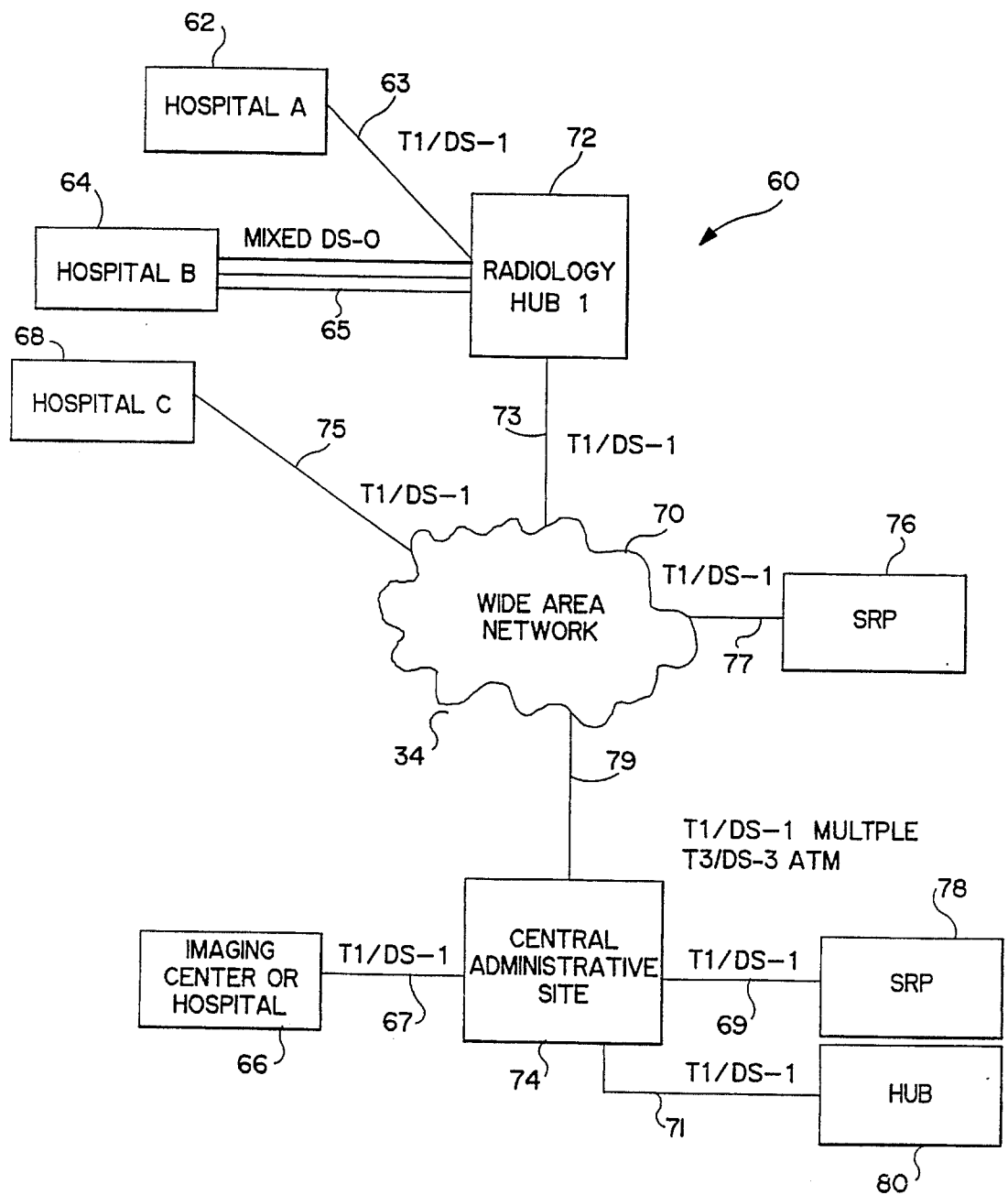
FIGS. 2A–2C are diagrams of another system for providing interpretation of radiological images to remote locations according to the invention.

For example, in FIG. 2A, Hospital A 62 is an acquisition site having a regional affiliation with Radiology Hub 1 72, and may opt for a point-to-point or multiplexed point-to-point connection 63 directly with Radiology Hub A, established via an intralata connection to a LEC.

In another example, Hospital C 68 may also have an affiliation with Radiology Hub 1 72, but may find that a direct point-to-point connection to Radiology Hub 1 through an LEC to be prohibitively expensive due to interlata tariffs, connection, or equipment costs. In this case it may be more cost effective for Hospital C to establish a direct link 75 with the IEC WAN 34 and connect to Radiology Hub A through the packet/cell switched network WAN 34 and connection 73 between Radiology Hub 1 and WAN 34.

The use of point-to-point LEC and packet and cell switched IEC digital communications circuits as described above, provides for a highly flexible radiology interpretation network architecture in which radiology images can be routed quickly, easily, and economically between any acquiring sites, radiology hubs, SRPs and Admin. Sites. This provides for an economically viable method of transmitting medical images (which are large in size) on a regional and national basis in a totally seamless way directed by a central (single or multipoint) Admin. Site.

At the interpretation sites, board-certified radiologists interpret the transmitted Studies by, for example, using workstations to view the images. The workstations generally utilize state-of-the-art technology and reproduce images at a resolution appropriate for making final interpretations, or alternatively the images may be printed by a laser camera film printer. If the radiologists need additional information, the Admin. Site will then contact the transmitting site (e.g., by telephone or electronic mail). Conference calling capabilities are also available.

After making an interpretation, the radiologist typically dictates a report of findings, has the dictation transcribed, reviews the transcribed report, and then signs the report, all coordinated by the Admin. Site. The report is then sent back across the Network to the acquiring site (e.g., by facsimile, remote print services, or electronic mail) and treated as any other medical test result by the medical record handling system at the acquiring site. A hardcopy of the report also may be sent by mail for confirmation.

In the disclosed embodiment, the acquiring sites produce digital data representative of radiological images, and the transferring of the digital data within the system 10 is performed by digital transmission. The long distance digital transmission of images, such as those between the radiology hubs and the SRPs, are performed using standard digital packet and cell switched WAN common carrier services. In FIG. 1, WAN 34 performing these services is represented by a cloud and can be any digital WAN common carrier service such as that offered by long distance carriers AT&T, SPRINT and MCI.

Throughout the system 10, the digital transmission is done with frames or packets or cells. That is, in general, all digital bits which represent an image are not sent at one time. Instead, the bits are broken into discrete portions (frames or packets), and these portions are sent separately to the receiver which reassembles them upon receipt. The particulars of the digital communication links which can be utilized in the system 10 are described below with reference to FIGS. 2A–2C.

In packet switching, a message is divided into packets which typically contain many bits each, and the message is transmitted packet-by-packet. Packet and cell switching all conform to one of four standard protocols: X.25; Frame Relay; SONET; and ATM. The appropriate standards for these protocols are known to those skilled in the art.

Digitization of a typical radiological hardcopy image (e.g., a conventional 14 inch by 17 inch x-ray film) results in approximately 10 Mbytes (i.e., 80 Mbits) of data, and in general, studies range in size from a few megabytes for ultrasound and nuclear medicine, to more than 100 megabytes for direct capture digital MR Studies. Thus, data generated is substantial for each Study that must be transferred across the network in a timely, cost efficient, and seamless manner.

Having generally described a system according to the invention, a more detailed description of the variety of possible communication links (and corresponding electronic hardware) which can be utilized in systems according to the invention will now be provided.

Systems according to the invention can use various digital communication links for transferring radiologic Studies among acquisition sites (e.g., the hospitals), radiology hubs, SRPs, and Admin. Sites. The digital links can include (i) T1/DS-1 carrier point-to-point services which operate at 1.544 Mbits/sec, (ii) DS-0 digital services which operate at 64 kbits/sec, (iii) DS-3 digital services which operate at 44,736 Mbits/sec, (iv) ATM and SONET links which operate at between 56 Mbits/sec and 2 Gbits/sec (v) Frame Relay links that operate at between 9,600 and 1,544,000 bits/sec., (vi) Ethernet or 802.3 LAN links which operate at 10 Mbits/sec, (vii) IEEE 802.6 standard metropolitan area networks (MANs), and (viii) ISDN (Integrated Services Digital Network) end-to-end services.

Systems according to the invention can use various software protocols for transferring medical images between the acquisition sites, regional hubs, SRP's and other locations. One such protocol, although not limited to this protocol, is referred to as TCP/IP (Telecommunications Control Protocol/Internet Protocol). This protocol makes it possible to divide the image into packets, and route these packets over a variety of communications equipment and services, resulting in image transmission with complete end-to-end file integrity. Other protocols may include Novel IPX, Appletalk, DECnet, or ISO.

Systems according to the invention can use networking equipment to physically connect and transmit the TCP/IP packets over the various network services. This equipment is selected, integrated, configured (special parameter settings for high volume image transmissions must be made), and managed by the Admin. Site. This equipment includes, but is not limited to, Ethernet Controllers on general purpose computers, bridge/routers, CSU/DSU's, multiplexers, network hubs, FDDI controllers and cables and ATM controllers and cables.

Referring to FIG. 2A, in another embodiment of the invention, a Radiology Healthcare Network 60 according to the invention includes image acquiring hospitals 62, 64, coupled to a regional radiology hub 72 and another image acquiring hospital 68 coupled directly to a digital packet switched WAN 70. Other elements of the system 60 include SRPs 76, 78 and another radiology hub 80.

As indicated, hospital 62 is coupled to radiology hub 72 by either a T1 or DS-1LEC channel 63. Hospital 64 is coupled to radiology hub 72 through four multiplexed DS-0 LEC channels 65, for a total available digital signaling rate of 256 kbit/sec. The multiplexed DS-0 channels are demultiplexed by equipment at the radiology hub 72.

Imaging center 66, SRP 78, and radiology hub 80 are each coupled to an Admin. Site 74 by either a T1 or DS-1LEC circuit 67, 69, and 71, respectively. Regional radiology hub 72, hospital 68 and SRP 76 are each coupled to the IEC WAN 70 over T1 or DS-1 channels 73, 75 and 77, respectively. The Admin. Site 74, which requires higher signaling rates due to the high image traffic expected to pass through the hub, can utilize multiple T1 or DS-1 channels 79, or a T3 or DS-3 channel, or a high data rate Asynchronous Transfer Mode (ATM) packet transmission technology.

Note that while particular coupling configurations are shown in FIGS. 1 and 2A, other configurations are possible which also result in systems capable of acquiring radiological images and transferring them to one or more distant sites for interpretation in accordance with the invention. However, irrespective of their physical network topology and combinations of circuits used, it becomes both seamless and transparent as to how the images are logically routed through the network.

Figure 2B:
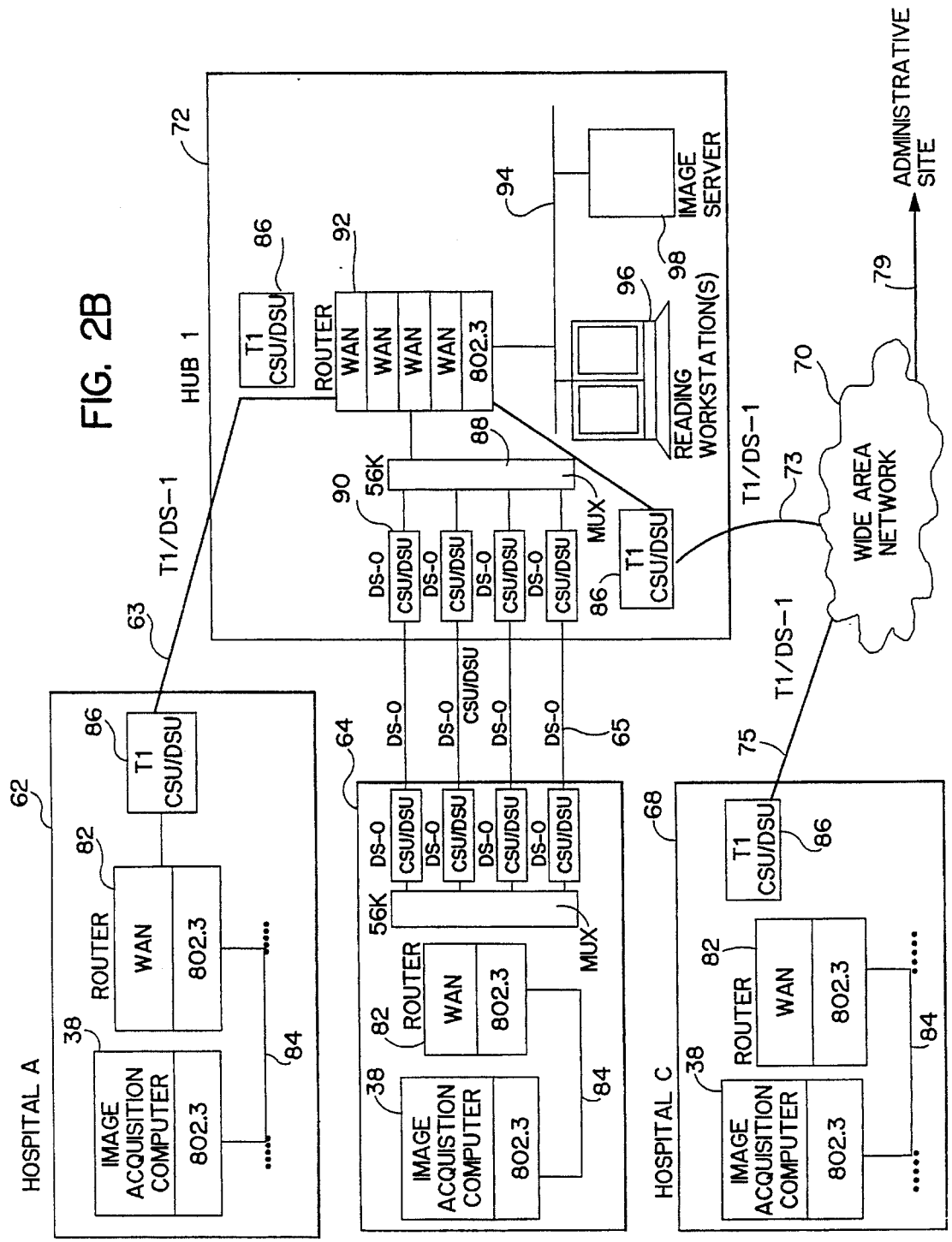

Referring to FIG. 2B, a more detailed diagram of a portion of FIG. 2A shows image communication hardware included in hospitals 62, 64, 68 and radiology hub 72. The hospitals include image acquisition equipment 38 coupled to a digital data router 82 via a local area network (LAN) 84 which conforms to the IEEE 802.3 standard. Router 82 in turn is connected to a WAN (or serial) interface which connects to T1 or DS-1 channel 86 which is then physically connected to the T1/DS1 63.

Regardless of the technique used to acquire the digital data representative of a radiological image, the digital data is then converted, by the image acquisition equipment 38, to, for example, an ACR-NEMA (American College of Radiology, and National Electrical Manufacturers Association) digital radiology image file format. In general, all components of the system according to the invention may adhere to the ACR-NEMA standard and are capable of manipulating (e.g., creating, storing, sending, receiving, writing, and reading) data in this format. That is, in the disclosed embodiment, the image acquisition equipment 38, image storing and routing equipment 98, and the image viewing equipment 96 can adhere to the ACR-NEMA standard. The ACR-NEMA standard is a well-documented, flexible, and open digital imaging-and communication standard which is likely to become an international standard for medical imaging. ACR/NEMA or DICOM is layered on top of the TCP/IP protocol suite. Other protocols, including proprietary vendor protocols are included in this invention.

Specific imaging, computer hardware, software, and networking equipment can be deployed to support the system defined herein. Equipment at each type of site is defined (but not limited to) as follows:

Acquisition Site:

Acquisition equipment 38 is deployed depending upon the image modality to be supported. For sites acquiring images from plain film, a film digitizer employing either laser or CCD technology is used to transfer the analog film data into an accurate digital representation of the data. An example of a film digitizer is a LUMISYS, manufactured by Lumisys, Sunnyvale, Calif. Digital film images are usually 10 Mbytes each. The digital data is then usually transferred from the film digitizer to a host computer via a high-speed interface such as SCSI or 84 IEEE 802.3. The host computer allows demographic input of patient and Study data to be logically combined with the image data, and then uses a network protocol (such as TCP/IP and/or ACR/NEMA or DICOM) to transmit the Study over the network. The image can be transferred from the 802.3 controller on the acquisition computer on an IEEE 802.3 LAN to an IEEE 802.3 port on a bridge/router 82. The bridge/router 82 then reformats the TCP/IP packet stream into the appropriate wide area protocol (examples are, but not limited to, HDLC, Point-To-Point or Frame Relay) and transmits the stream to the CSU/DSU 86, which then synchronizes and transmits the stream to the appropriate circuit.

For acquisition sites supporting computed radiography, the charged phosphor plate common to this modality is inserted into a computed radiography reading computer, which then converts the phosphor image into a digital representation. The image is transferred to a host computer via a high-speed interference such as SCSI or 802.3. The host computer allows demographic input of patient and Study data to be logically combined with the image data, and then uses a network protocol (such as TCP/IP and/or ACR/NEMA or DICOM) to transmit the Study over the network. The image can be transferred from the IEEE 802.3 controller on the acquisition computer on an IEEE 803.3 LAN to a IEEE 802.3 port on a bridge/router 82. The bridge/router 82 then reformats the TCP/IP packet stream into the appropriate wide area protocol (examples are, but not limited to, HDLC, Point-To-Point or Frame Relay) and transmits the stream to the CSU/DSU, which then transmits the stream to the appropriate circuit.

For those sites supporting MR, CT, ultrasound, and nuclear medicine imaging, one method of obtaining the images is via a video (or commonly referred to as "frame grabber") interface. These interfaces include a computer acquisition board which has an input the video signal from these modalities. The board creates a digital representation of the video signal and stores it on the acquisition computer system. The host computer allows demographic input of patient and Study data to be logically combined with the image data, and then uses a network protocol (such as TCP/IP and/or ACR/NEMA or DICOM) to transmit the Study over the network. The image can be transferred from the IEEE 802.3 controller on the acquisition computer on an IEEE 802.3 LAN to a IEEE 803.3 port on a bridge/router 82. The bridge/router 82 then reformats the TCP/IP packet stream into the appropriate wide area protocol (examples are, but not limited to, HDLC, Point-To-Point or Frame Relay) and transmits the stream to the CSU/DSU 86, which then transmits the stream to the appropriate circuit.

MR and CT scanners may also be connected in this system via direct digital interfaces. Direct digital interfaces move the images and patient and demographic data from the scanner to the network, or to another general purpose computer which may reformat the images into another organization of network protocol. The image can be transferred from the IEEE 803.3 controller on the acquisition computer on an IEEE 802.3 LAN to a IEEE 802.3 port on a bridge/router 82. The bridge/router 82 then reformats the TCP/IP packet stream into the appropriate wide area protocol (examples are, but not limited to, HDLC, Point-to-Point or Frame Relay) and transmits the stream to the CSU/DSU 86, which then transmits the stream to the appropriate circuit.

Acquiring sites may have a dedicated T1/DS-1 63 connected to either a radiology hub 72 or directly to the packet/cell switched WAN via a T1/DS-1 75. In addition, based upon whether the acquiring location is within the same lata as the regional hub, and the network bandwidth requirements are not significant (greater than 256k bits/second), multiple DS-0 65 circuits can be multiplexed together to form and present to the WAN port on the bridge/router 92 a single 256 bit/second circuit.

Regional Radiology Hub:

Equipment at a regional radiology hub 72 can include networking components 86, 88, 90, 92, 94, and cabling, high-resolution image viewing workstations 96, laser camera based film printer digitizer, and perhaps a file server 98 (referred to as an Image Router).

Network components consist of a multiple WAN port bridge/router 92 with a LAN port supporting IEEE 802.3, or other higher speed LAN protocols. CSU/DSU's 86 will also be used to support each physical circuit. For those regional hubs with Hospitals connecting via multiplexed DS-0 circuits 65, a network multiplexer 88 will be used.

Regional radiology hubs may be directly connected to the WAN 70 by either a dedicated direct T1/DS-1, T3, DS-3, or ATM connection to the Admin. Site, or by a T1/DS-1, TC/DS-3, or an ATM connection to the Wide Area Packet/Cell switched network 73.

Most radiologic interpretations will be performed on high-resolution image viewing workstations 96. High resolution workstations consist of a general purpose computer (i.e. Macintosh, or IBM-PC Compatible, or RISC Omp) continuing at least a few hundred megabytes to a few Gbytes of magnetic storage, main memory, specialized graphics display boards, and from 1 to 8 high resolution grey-scale or color monitors. For example, suitable image viewing equipment includes equipment commercially available, but not limited to, Kodak Health Imaging Systems of Richardson, Tex. such as the Personal Display System (PDS). The workstation 96 can be an Apple Quadra 950, Quadra 800, or Centris 650 running MAC OS 7.x. The workstation can include a local hard disk having, for example, 230 Mbytes to 5.2 Gbytes capacity and video display card having, for example, 16 Mbytes of capacity. Monitors associated with the workstation can include 1.2 k by 1.6 k resolution displays with 16-bit mapped to 8-bit via LUT (Loan Up Table) and having a 60 Hz scan rate and/or 2 k by 2.5 k resolution displays with 16-bit mapped to 8-bit via LUT and having 65 Hz scan rate. Printers can include laser film printers such as the Kodak Ektascan Laser Printer Model 2180, the 3M Laser Imager Model P831, the 3M Laser Imager Plus Model M952, and the Agfa/Matrix Compact L Printer.

In addition, a regional radiology hub can support significant image volumes and be configured with a file server 98. A file server 98 consists of a general purpose computer with sufficient magnetic and/or optical storage usually from 1 to 20 Gbytes. A file server also consists of a network operating system and application software to allow the transparent routing of images from the WAN to the LAN.

SRP:

Equipment at an SRP can include network components and medical imaging high resolution image viewing workstations, laser camera based film printers, and perhaps a file server.

Network components consist of multiple wide area network port bridge/routers 86 with a LAN port supporting IEEE 802.3 or other higher speed LAN protocols. CSU/DSU is well also be used to support each physical circuit.

SRP's may be directly connected to the WAN by either a dedicated direct T1/DS-1, T3, DS-3, or ATM connection to the Admin. Site, or by a T1/DS-1, TC/DS3, or an ATM connection to the Wide Area Packet/Cell switched network.

Most radiologic interpretations will be performed on high-resolution image viewing workstations. High resolution workstations consist of a general purpose computer (i.e. Macintosh, or IBM-PC Compatible, or RISC Omp) continuing at least a few hundred megabytes to a few Gbytes of magnetic storage, main memory, specialized graphics display boards, and from 1 to eight high resolution grey-scale or color monitors. For example, suitable image viewing equipment includes equipment commercially available but not limited to Kodak Health Imaging Systems of Richardson, Tex. such as the Personal Display System (PDS). The workstation 58 can be an Apple Quadra 950, Quadra 800, or Centris 650 running MAC OS 7.x. The workstation can include a local hard disk having, for example, 230 Mbytes to 5.2 Gbytes capacity and video display card, having, for example, 16 Mbytes of capacity. Monitors associated with the workstation can include 1.2 k by 1.6 k resolution displays with 16-bit mapped to 8-bit via LUT (Loan Up Table) and having a 60 Hz scan rate and/or 2 k by 2.5 k resolution displays with 16-bit mapped to 8-bit via LUT and having 65 Hz scan rate. Printers can include laser film printers such as the Kodak Ektascan Laser Printer Model 2180, the 3M Laser Imager Model P831, the 3M Laser Imager Plus Model M952, and the Agfa/Matrix Compact L Printer.

In addition, an SRP can support significant image volumes and be configured with a file server. A file server consists of a general purpose computer with sufficient magnetic and/or optical storage usually from one to 20 Gbytes. A file server also consists of a network operating system and application software to allow the transparent routing of images from the WAN to the LAN.

Admin. Site:

The Equipment at the Admin. Site 74 consists of network circuits, networking components and cabling, file server(s), RAID and/or optical storage devices, PACS or Teleradiology software, an administrative database computer 117, and a Study tracking mechanism.

Circuits to the WAN include single T1/DS-1, multiple T1/DS-1, T3/DS-3, or ATM connections 79 to the IEC packet/cell switched network, and any additional of the aforementioned circuits required to accomplish direct wide area connections to either SRP's, radiology hub's, or other acquiring hospitals.

Networking equipment consists of high speed bridge/routing hubs 100 (for example, the Cisco 7000, manufactured by Cisco Systems, Menlo Park, Calif.) which provide backbone bandwidth in aggregate of 500 Mbits/second. This bridge/router 100 has multiple WAN ports capable of handling wide area connection circuits of varying speeds. The bridge/router 100 also has a LAN connection 106 to a high-speed backbone 110 supporting either IEEE 803.3, the proposed "Fast Ethernet" protocol, FDDI, and/or ATM, although other high-speed LAN technologies could also be used as they are developed. Of course, each separate physical wide area circuit needs the appropriate CSU/DSU 86, 102, 104 or other modem.

Connected to the high speed LAN 110 is a file (image) server(s) 112 with attached RAID device 114 to allow high throughput file read/write operations (from 4 to 100 megabytes/sec.), and/or optical storage devices to allow permanent archiving of medical images. Optical tape units could also be used.

PACS or Teleradiology software, provided by existing vendors, allows for the routing of images to either radiology hubs or SRP's. This software operates at a layer above the network protocol, although it is possible for the network protocol (e.g., the TCP/IP suites as Networked File Server of the File Transfer Protocol, or Novel IPX/SPX) to allow the images to be distributed without any additional PACS or Teleradiology software used.

The administrative database computer 117 can be use to manage the radiology resources on the Network and be used to make many of the Study routing decisions based on the Study parameters and the available resources. A tracking mechanism, either electronically based or manually based can be used to track and monitor the progression of Studies on the network. In addition, an Admin. Site may also have high resolution image stations.

The following more specifically, describes various equipment used in acquiring sites, hubs, and SRPs. The image storage and routing equipment can include an image server 112 (Admin. Site 74 of FIG. 2C) having one or more storage units 114. The storage units 114 can include magnetic and/or optical disks. Suitable image storage and routing equipment includes equipment commercially available from a variety of vendors. Such vendors may include (but are not limited to) Kodak Health Image Services ("KHIS"), AVP/E-Systems, Images On-Call or Radman. The KHIS equipment can include a SUN workstation running, for example, SUN OS 4.1.x or SUN Solaris 1.x or 2.x and the DBMS database management tool from Sybase. The Kodak equipment can include the Ektascan Model 6800 Automated Disk Library which uses 14 inch optical disks, the Model 560 Automated Disk Library which uses 5.25 inch optical disks, the standalone 14 inch optical disk drive, and the stand-alone 5.25 inch optical disk drive. The optical disk units can be "jukeboxes" which typically provide at least about 1 terabyte storage capacity (where tera is the prefix for $1 \times 10^{12}$). The storage units also can include RAID (Redundant Arrays of Inexpensive Disks) technology. The SUN workstation can be interfaced with the storage units via a Small Computer Serial Interface (SCSI) port. Data compression may or may not be used in the storage of data.

The image viewing equipment 116 can include a reading workstation capable of displaying gray scale or color radiological images on a CRT display, and/or printing hardcopies of the radiological images that are acquired and sent by the image acquisition equipment 38 and/or that are stored, retrieved, and sent by the image server 112. In general, suitable image acquisition equipment 38, image server 112, and image viewing equipment 116 is commercially available from multiple vendors including Vortech Data, Inc. of Richardson, Tex. and Eastman Kodak Company of Rochester, N.Y. under the product name Imagelink.

Each radiological image acquiring site includes at least image acquisition equipment 38. The acquiring sites (e.g., the hospitals) typically also include an image server 112 and/or image viewing equipment 116. At a minimum, the interpreting sites (e.g., the hubs and the SRPs) include the image viewing equipment 116, but they typically also include the image acquisition equipment 38 and/or the image server 112.

Acquisition of a digital data representative of a radiological image can be accomplished by the image acquisition equipment 38 in a variety of ways. For example, radiographic film (i.e., an x-ray image on film) can be converted to a digital image (digitized) using a film digitizer. The film digitizer can be controlled by a computer workstation such as a SUN SPARC or a SUN IPC, available from SUN Microsystems. Workstations can be used to manipulate, format, store, and transmit the digitized image output from the film digitizer, i.e., act as an intelligent interface between the digitizer and the radiology network. While a variety of configurations for the workstation are possible, the workstation, if a SUN IPC, can be configured with an 876 Mbyte hard disk and 36 Mbytes of internal random access memory (RAM). The SUN IPC can run the SUN operating system (OS) 4.1.x or the SUN Solaris 1.x or 2.x. The film digitizer 44 can be a Lumiscan (model 150 or model 200) which is available from Lumisys of Sunnyvale, Calif.

Another technique for acquiring the digital data is by directly capturing and digitizing video images (without first reducing them to hardcopy) from the image acquiring equipment. Video image capture/digitization is useful with computed tomography (CT), magnetic resonance imaging (MRI), nuclear medicine, and ultrasound imaging because each of these techniques produces video images as a standard output format. Commercially available "frame grabbing" electronics can be used to capture and digitize the video images. In general, the frame-grabbing electronics are contained in or coupled to a host computer platform 50 such as a SUN platform. A typical configuration for the platform includes local storage capacities of from about 0.5 Gbytes to 6 Gbytes. The platform can run the SUN OS 4.1.x or the SUN Solaris 1.x or 2.x. The frame-grabbing electronics can have 8-bit or 12-bit digital capture capability.

As another example, some image acquiring equipment provide digital representations that can be accessed directly (i.e., without first creating a hardcopy or a video image and then digitizing the hardcopy or video image) by commercially available hardware. Such digital representations of an acquired image are typically presented after the acquiring system has performed post-processing on the acquired image, and is presented in a standard digital radiological image format.

Figure 2C:
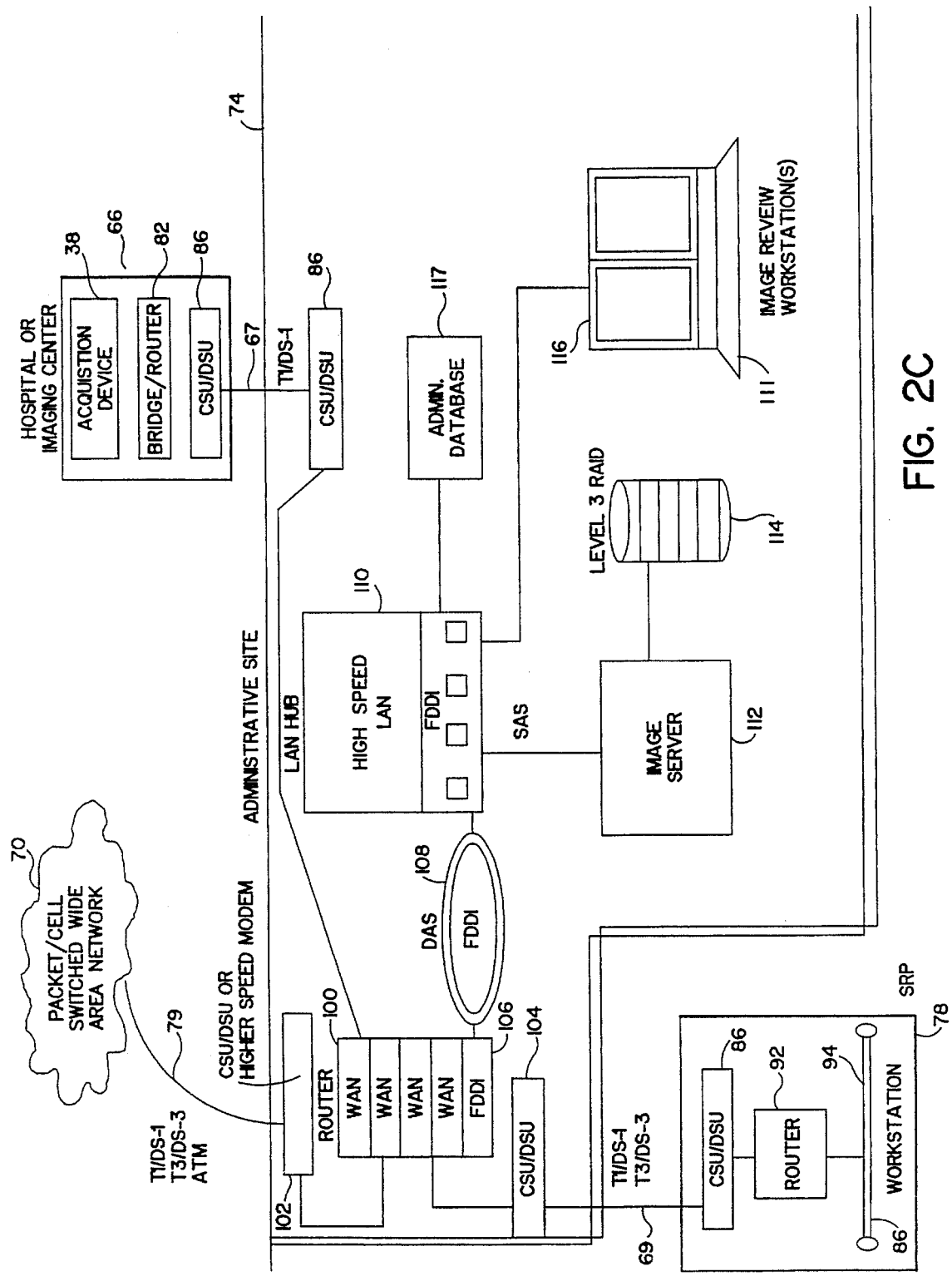

The routers 82 and 92 of FIG. 2B and the router 100 of FIG. 2C can be commercially available routers from, for example, Cisco Systems, Inc. of Menlo Park, Calif.

Other modifications and implementations will occur to those skilled in the art without departing from the spirit and the scope of the invention as claimed. Accordingly, the invention is to be defined not by the preceding illustrative description, but by the following claims.

What is claimed is:

1. A method for interpreting radiological images, comprising:
    a) generating a radiological image at an image acquiring site;
    b) creating a radiology study which includes the image and identifying information about the study;
    c) digitally transmitting the identifying information about the study over a wide area network to a digital processing system at an administrative site for determination of radiological study parameters from the identifying information, and selection of an interpretation site based on the study parameters and information stored at the administrative site relating to each of a plurality of interpretation sites;
    d) digitally transmitting the study over a wide area network to an interpretation site in response to a command signal from the administrative site; and
    e) receiving an interpretation of the study at a site determined by the administrative site.

2. The method of claim 1, wherein the study first is transmitted from the acquiring site to the administrative site in response to the command signal.

3. The method of claim 2, wherein the study is transmitted from the administrative site to the interpretation site.

4. The method of claim 1, wherein the study is transmitted from the acquiring site directly to the interpretation site in response to the command signal.

5. The method of claim 1, wherein the identifying information includes patient information such as age, sex, or other demographic information, suspected pathology, modality, anatomy and location of the site where the radiological image acquisition was performed.

6. The method of claim 1, wherein the information relating to the interpretation sites includes information relating to the availability of medical providers, their hours of coverage, and the existing backlog at the interpretation site.

7. The method of claim 1, wherein the administrative site monitors the progress of the interpretation of the study by the interpretation site.

8. The method of claim 7, wherein the administrative site monitors the interpretation site for timeliness.

9. The method of claim 7, wherein the administrative site monitors the interpretation site for requests for additional images or identifying information.

10. The method of claim 1, wherein the administrative site monitors the time during which the interpretation site is generating an interpretation of the study, and if the time monitored is greater than a predetermined time allotted for interpretation, the study is transmitted to a different interpretation site.

11. A method for interpreting radiological images comprising:
    a) providing a digital processing system for use at an acquiring site for: (i) generating a study containing one or more radiological images, (ii) generating identifying information about the study, and (iii) transmitting the study and the identifying information over a wide area network;
    b) providing a digital processing system for use at an administrative site for: (i) receiving the study and identifying information over the wide area network, (ii) storing information relating to a plurality of image interpretation sites which are coupled to the wide area network, (iii) performing a comparison between the identifying information and the information relating to the image interpretation sites, (iv) using the comparison to select an image interpretation site, and (v) controlling the routing of the study to the interpretation site over the wide area network; and
    c) providing a digital processing system at an image interpretation site for: (i) receiving a study over the wide area network, (ii) displaying the study on a high-resolution image viewing system, (iii) generating a report relating to the study and (iv) transmitting the report over the wide area network to a site determined by the administrative site.

12. The method of claim 11, further comprising prompting a user at the acquiring site to enter identifying information relating to patient and study demographics such as age, sex, other demographic information, suspected pathology, modality, anatomy and the location of the acquiring site where the radiological image acquisition was performed.

13. The method of claim 12, wherein the administrative site prompts the acquiring site to initiate transfer of the study to the administrative site.

14. The method of claim 12, wherein the administrative site prompts the acquiring site to initiate transfer of the study to the interpretation site.

15. The method of claim 11, wherein the information relating to the plurality of interpretation sites comprises information about the availability of medical providers, hours of their coverage, and existing backlog at the site.

16. The method of claim 11, further comprising prompting a user at the interpretation site to enter data relating to an interpretation of the study.

17. The method of claim 11, wherein the digital processing system for use at the administrative site monitors the generation of the report at the interpretation site for timeliness.

18. The method of claim 17, wherein the digital processing system transmits the study to a different interpretation site when generation of the report appears untimely.

19. The method of claim 17, wherein the digital processing system monitors the interpretation site for requests for additional images or information.

20. A method for providing interpretation of radiological images, comprising: using a wide area network to communicate between: (i) a data processing system located at an administrative site, (ii) digital transmission equipment located at a plurality of image acquiring sites for transmitting onto the wide area network digital radiological images and identifying information relating to a study performed at the acquiring site, and (iii) digital receiving equipment located at a plurality of image interpretation sites for receiving the digital radiological images and identifying information; wherein the data processing system at the administrative site receives identifying information about a study from one of the acquiring sites, determines study parameters from the identifying information, compares the study parameters with information stored at the administrative site relating to the plurality of image interpretation sites, selects an interpretation site for interpretation of the study, and controls the routing of the study from the acquiring site to the interpretation site for interpretation of the study; and wherein the interpretation site generates a report about the study and transmits the report over the wide area network to the acquiring site that generated the study.

21. A system for providing interpretation of radiological images, comprising:

at least one image-acquiring site comprising: (i) acquisition equipment for obtaining images, (ii) a host computer for creating a study comprising patient information and the images, (iii) networking equipment for routing the study over a wide area network;

an administrative site coupled to at least one image acquiring site by a wide area network, comprising: (i) a data processing system for: receiving the study, selecting an interpretation site based on a determination of radiological parameters from the patient information, initiating transmission of the study to the selected interpretation site, and monitoring the progress of an interpretation at the interpretation site, and (ii) networking equipment for transmitting the study to a selected interpretation site; and at least one interpretation site coupled to the administrative site by a wide area network, comprising: (i) a high-resolution image viewing workstation for viewing the study, (ii) a computer for generating an interpretation of the study, and (iii) networking equipment for routing the interpretation under the control of the administrative site.

22. A method for interpreting radiological images, comprising:

(a) generating a radiological image at an image-acquiring site;

(b) creating a radiological study which includes the image and identifying information about the study;

(c) at an administrative site coupled with the image-acquiring site, selecting an interpretation site based on study parameters and information stored at the administrative site;

(d) digitally transmitting the study over a wide area network to an interpretation site in response to a command signal from the administrative site; and (e) receiving an interpretation of the study at a site determined by the administrative site.

* * * * *

(12) EX PARTE REEXAMINATION CERTIFICATE (7083rd)
United States Patent
Pinsky et al.

(10) Number: US 5,513,101 C1
(45) Certificate Issued: Sep. 29, 2009

(54) RADIOLOGICAL IMAGE INTERPRETATION APPARATUS AND METHOD

(75) Inventors: Howard Pinsky, Mansfield, MA (US); Scott S. Sheldon, Boston, MA (US); Nicholas A. Christakis, Philadelphia, PA (US); Michael Schmertzler, New Caanan, CT (US)

(73) Assignee: EMED Technologies Corporation, Lexington, MA (US)

Reexamination Request:
No. 90/010,027, Sep. 14, 2007
No. 90/009,052, Feb. 25, 2008

Reexamination Certificate for:
Patent No.: 5,513,101
Issued: Apr. 30, 1996
Appl. No.: 08/474,374
Filed: Jun. 7, 1995

Related U.S. Application Data

(63) Continuation of application No. 08/158,140, filed on Nov. 26, 1993, now Pat. No. 5,469,353.

(51) Int. Cl.
*G06F 19/00* (2006.01)

(52) U.S. Cl. .......................................... 705/3; 706/924
(58) Field of Classification Search ........................ None
See application file for complete search history.

(56) References Cited

PUBLICATIONS

Medical Diagnostic Imaging Support System, Specification: issued by the US Army Engineering Division, Huntsville, Alabama, Solicitation #DACA87–90–R–0058, Amendment 0009, Jun. 14, 1991.

William J. Chimiak, "The Digital Radiology Environment," IEEE Journal on Selected Areas of Communication, vol. 10, No. 7, Sep. 1992, pp. 1133–1144.

"The Digital Radiology Environment" by William H. Chimiak, IEEE Journal on Selected Areas of Communication, vol. 10, No. 7, Sep. 1992 (hereinafter "the Chimiak article").

Keynote Address: Image Management and Communication (IMAC) in Patient Care: New Technologies for Better Patient Care, Seong K. Mun Second International Conference, 1991, Publication Date: Apr. 10–13, 1991 (hereinafter "the Mun address").

*Primary Examiner*—Linh Nguyen

(57) ABSTRACT

A Radiology Healthcare Network provides high quality, timely medical interpretations of radiological images on a national (e.g., across the U.S.) and regional basis. The images can include images created by conventional x-ray technology, computed radiography, magnetic resonance imaging (MRI), computed tomography (CT), ultrasound imaging, nuclear medicine, and mammography equipment. The invention includes the acquisition of these images from health care facilities, the conversion of these images to digital format, the routing of these converted images, the interpretation of these routed images, and the routing of the interpretations back to the originating facility. The images are routed-(e.g., on a variety of high-speed digital and analog telecommunication networks) to the appropriate interpretation resource by an administrative site on the Network based on one or more requirements associated with the radiological study. The interpretation can be performed on high-resolution workstations and/or on films produced by film printers. The invention can include quality control measures which assure high image and interpretation quality. The control and tracking of images by the administrative site results in the production of a complete, signed interpretive report in a timely manner.

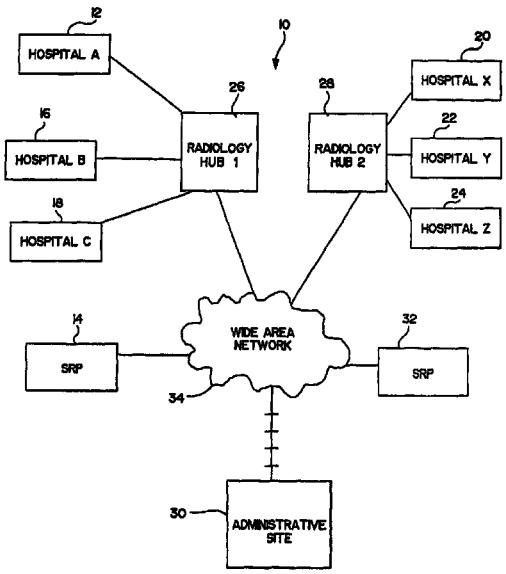

EX PARTE REEXAMINATION CERTIFICATE ISSUED UNDER 35 U.S.C. 307

THE PATENT IS HEREBY AMENDED AS INDICATED BELOW.

AS A RESULT OF REEXAMINATION, IT HAS BEEN DETERMINED THAT:

Claims 1–22 are cancelled.

* * * * *